(12) United States Patent
Zheng et al.

(10) Patent No.: US 11,332,766 B2
(45) Date of Patent: May 17, 2022

(54) **STRAIN OF *SERRATIA LIQUEFACIENS* AND A METHOD OF PRODUCING HELIOTROPIN WITH THE SAME STRAIN**

(71) Applicant: XIAMEN OAMIC BIOTECHNOLOGY CO., LTD., Xiamen (CN)

(72) Inventors: Pu Zheng, Xiamen (CN); Zhimin Deng, Xiamen (CN); Pengcheng Chen, Xiamen (CN); Xijing Zhao, Xiamen (CN); Mingtao Zhao, Xiamen (CN); Chenguang Xing, Xiamen (CN)

(73) Assignee: XIAMEN OAMIC BIOTECHNOLOGY CO., LTD., Xiamen (CN)

( * ) Notice: Subject to any disclaimer, the term of this patent is extended or adjusted under 35 U.S.C. 154(b) by 781 days.

(21) Appl. No.: 16/090,748

(22) PCT Filed: Apr. 1, 2017

(86) PCT No.: PCT/CN2017/079320
§ 371 (c)(1),
(2) Date: Oct. 2, 2018

(87) PCT Pub. No.: WO2017/197993
PCT Pub. Date: Nov. 23, 2017

(65) Prior Publication Data
US 2021/0317489 A1 Oct. 14, 2021

(30) Foreign Application Priority Data
May 17, 2016 (CN) .......................... 201610327227.6

(51) Int. Cl.
C12P 17/04 (2006.01)
C12N 1/20 (2006.01)
C12R 1/425 (2006.01)

(52) U.S. Cl.
CPC .............. *C12P 17/04* (2013.01); *C12N 1/205* (2021.05); *C12R 2001/425* (2021.05)

(58) Field of Classification Search
CPC ....................................................... C12P 17/04
See application file for complete search history.

(56) References Cited

FOREIGN PATENT DOCUMENTS

| CN | 105503814 A | 4/2016 |
| CN | 105779363 A | 7/2016 |

OTHER PUBLICATIONS

Santos et al., "Microbiologic oxidation of isosafrole into piperonal," Applied Biochemistry and Biotechnology 107:649-657, 2003.*

(Continued)

*Primary Examiner* — Rosanne Kosson
(74) *Attorney, Agent, or Firm* — Cooper Legal Group, LLC

(57) ABSTRACT

The present invention provides a bacterium and a method for the biological production of Heliotropin by the fermemtation of safrole. In one aspect of the present invention, a process for the conversion of safrole to Heliotropin is achieved by the use of a bacterial strain of *Serratia liquefaciens* ZMT-1 (CCTCC M 2016170). The production method comprises the steps of seeding the *Serratia liquefaciens* culture in the presence of oxygen for 24-36 hours, transforming the safrole substrate for 24-48 hours with 0.5-3 g/L substrate concentration, and reaching the Heliotropin concentration of 160-524 mg/L. The present invention reports, for the first time, on a method for producing the high concentration of Heliotropin by using the *Serratia liquefaciens* ZMT-1 strain or the enzyme extracted from the strain.

10 Claims, 2 Drawing Sheets
Specification includes a Sequence Listing.

(56) References Cited

OTHER PUBLICATIONS

Nicholson et al., Complete Genome Sequence of Serratia liquefaciens Strain ATCC 27592, Genome Announcements, Aug. 31, 2013, vol. 1, issue 4, p. 1.
Tang et al., Research Development of Synthesis of Heliotropin, Guangzhou Chemical Industry, Aug. 31, 2010, vol. 38, issue 8, pp. 59-86.
"Serratia liquefaciens Strain ZMT-1 16S Ribosomal RNA Gene, Partial Sequence", GenBank, accession No. KU999993.1, Apr. 23, 2016.

* cited by examiner

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
agagtttgat cctggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthesized

<400> SEQUENCE: 2
ggttaccttg ttacgactt                                               19
```

STRAIN OF *SERRATIA LIQUEFACIENS* AND A METHOD OF PRODUCING HELIOTROPIN WITH THE SAME STRAIN

FIELD OF THE INVENTION

The present invention relates to a bacterial strain of *Serratia liquefaciens* ZMT-1 (CCTCC M 2016170), and a method of converting and synthesizing Heliotropin, in the field of biotechnology.

BACKGROUND OF THE INVENTION

Heliotropin, also known as piperonal, has the chemical name of 3,4-dioxymethylene benzaldehyde. The molecular formula is $C_8H_6O_3$ and the molecular weight of Heliotropin is 150.14 g·mol$^{-1}$ respectively. In the mid 19th century, Rud. Fittig and W. H. Mielch found the substance in a study of the hydrolysis of the alkaloid piperine. Heliotropin is widely found in essential oils, violets, camphor wood and acacia, having an aroma similar to sunflower and cherry. Heliotropin also has a strong sweetly floral taste, spicy and bitter. Heliotropin is one of the world's main flavors as well as one of the most attractive fragrances.

In the fragrance and flavor industry, Heliotropin may be used as a starting material to prepare helional, piperonyl acetone, piperonylonitrile, etc, all of which are widely used in cosmetics such as perfumes. In medicine, Heliotropin can be used as raw materials to prepare intermediates for the antihypertensive, cerebrovascular and anti-cancer drugs. In agriculture, Heliotropin may be utilized as a starting material to prepare aldehyde synergist and other synergistic agents. In industry, Heliotropin is often used as a polishing agent. In the 90s, the world annual production of Heliotropin is about 550 tons, mainly produced by three countries: China, Japan and Spain. By 2012, the world annual output of Heliotropin reached 1,100 tons, and the world's demand for Heliotropin has been increasing each year.

At present, the industrial production of Heliotropin is mainly through semi-synthesis with safrole as a raw material or full synthesis with catechol as a raw material. The synthetic processes are both mature, but they suffer from problems of serious environmental pollution and high-energy consumption. As people become more concerned with the process of material production and the requirements of European countries and the United States to food additives, spices produced via biological fermentation and enzymatic production are considered natural flavor and are increasingly popular. However, at this stage, there is no report of the large-scale production of Heliotropin by a biological method in the industry.

SUMMARY OF THE INVENTION

The first technical problem to be solved by the present invention is to provide a strain of microorganism capable of converting safrole to Heliotropin. The microbial strain is a *Serratia liquefaciens* ZMT-1.

The *Serratia liquefaciens* ZMT-1 strain has been deposited at the China Center for Type Culture Collection since 5 Apr. 2016, under the accession number CCTCC NO: M 2016170 and the address is Wuhan University, Wuhan, China.

When plated on a basic inorganic salt medium plate, the colonies of the *Serratia liquefaciens* ZMT-1 are pale white, translucent and viscous, with a raised center and smooth edge, and the colonies are about 1 mm in diameter. Electron microscopy shows that the cells of the *Serratia liquefaciens* ZMT-1 are straight rod-shaped and apex obtuse. The cells of the *Serratia liquefaciens* ZMT-1 do not sporulate and do not form a capsule, but the cells have flagella, and the size of the cells is (0.5~0.8) μm×(0.5~2.0) μm. The *Serratia liquefaciens* ZMT-1 is facultative aerobic and Gram-negative. The *Serratia liquefaciens* ZMT-1 grow in the conditions of the temperature range of 10~37° C., of the pH 4-9, and of the NaCl range of 0%~4%. The *Serratia liquefaciens* ZMT-1 is able to utilize glucose, sucrose, mannitol, fructose, maltose and glycerol as carbon sources, as well as ammonium salts, nitrates, yeast power, peptone and other complex sources of nitrogen.

The above-mentioned basic inorganic salt culture medium contains 1 g/L ammonium nitrate, 0.5 g/L magnesium sulfate heptahydrate, 0.5 g/L ammonium sulfate, 0.5 g/L potassium dihydrogen phosphate, 1.5 g/L dipotassium hydrogen phosphate and 0.5 g/L sodium chloride. The pH of the said basic inorganic salt culture medium is 7.0.

The method for culturing the *Serratia liquefaciens* ZMT-1 strain is that the original strain is inoculated into a culture medium slant and grow for 1-2 days at 25-37° C. for activation. After activation, the strain is inoculated into a seed culture medium and allowed to propagate in the said seed culture medium for 24~36 hours, at 25~37° C. and a shaking speed of 150~220 rpm. The said seed culture medium is comprised of 1% peptone, 0.5% yeast powder, 1% sodium chloride and 1% glucose, and the pH of the said seed culture medium is neutral.

The second technical problem to be solved in the present invention is to provide a method of applying the *Serratia liquefaciens* ZMT-1 for producing Heliotropin by biotransformation using safrole as a raw material.

In one embodiment of the present invention, the seed liquid, which contains the propagated *Serratia liquefaciens* ZMT-1 in the seed culture medium, is inoculated into a fermentation medium at a volume ratio of 2%~10%. The fermentation medium has a liquid volume of 10% to 40% in respect to a bioreactor. Under the conditions of the culture temperature of 22-37° C. and of the rotation speed of 150-220 rpm, the *Serratia liquefaciens* ZMT-1 strain is cultured for 24~36 hours, after which the safrole substrate is added to the fermentation medium. The *Serratia liquefaciens* ZMT-1 strain in the fermentation medium is then allowed to convert the substrate for 24~48 hours with the same temperature and the same rotation speed.

In one embodiment of the present invention, the fermentation medium contains 0.5-1 g/L of ammonium nitrate, 0.1-0.5 g/L of magnesium sulfate heptahydrate, 0.1-0.5 g/L of ammonium sulfate, 0.5-1.5 g/L of dipotassium hydrogen phosphate, 0.1-0.5 g/L of sodium chloride, 0.1-1 g/L of yeast powder and 3-20 g/L of glucose. The pH of the fermentation medium is 6.8 to 7.5. In one aspect, the glucose in the fermentation medium can be replaced with fructose, mannitol, sucrose, glycerol or maltose. The concentration of the safrole substrate is 0.5~3 g/L.

In one embodiment of the present invention, the *Serratia liquefaciens* ZMT-1 seed liquid is inoculated to the fermentation medium at a volume ratio of 5%. The fermentation medium has a loading volume of 20%. Under the conditions of 30° C. fermentation temperature and 180 rpm rotation speed, the *Serratia liquefaciens* ZMT-1 strain is cultured for 24~36 hours. After which, the safrole substrate is added to the fermentation medium and is converted to Heliotropin by the *Serratia liquefaciens* ZMT-1 at the same temperature and the same rotation speed. The conversion of safrole to Heliotropin takes 48 hours.

In one embodiment of the present invention, after the conversion of safrole to Heliotropin is finished, 5 to 50 g of wet resin is added to per 100 mL of the conversion system. The resin is macroporous resin XAD-2 or HZ-802, and the mixture is shock-adsorbed for 30 to 60 minutes. The resin is filtered out and the filtrates are eluted with ethyl acetate of 1-2 times the resin volume. The eluted filtrates are dehydrated with anhydrous sodium sulfate. The dehydrated filtrates are concentrated in vacuum at 30-50° C. and left to crystallize in a 4° C. refrigerator.

The present invention screens a ZMT-1 strain of *Serratia liquefaciens* from the soil. The *Serratia liquefaciens* ZMT-1 strain has a wide conversion temperature range of 22-37° C. and mild reaction conditions and is able to utilize complex nitrogen sources such as yeast powder. The *Serratia liquefaciens* ZMT-1 strain is capable of producing a high concentration of Heliotropin (160~500 mg/L) in a short time. The invention has a good prospect.

Biological Material Preservation

The *Serratia liquefaciens* ZMT-1 strain has been deposited at the China Center for Type Culture Collection since 5 Apr. 2016, under the accession number CCTCC NO: M 2016170 and the address is Wuhan University, Wuhan, China.

DETAILED DESCRIPTION (GC-MS) analysis of the product. Two ml of the conversion solution was centrifuged for analysis. The supernatant was collected and filtered through 0.45 μm microporous membrane into the liquid phase. Alternatively, Two ml of the conversion solution was extracted with equal volume of ethyl acetate. The mixture was left to precipitate, after which the upper organic phase was collected and treated with anhydrous sodium sulfate to remove excess water. The treated organic phase was filtered through a 0.45 μm organic filter membrane. The filtrate was analyzed by gas chromatography-mass spectrometry (GC-MS). The GC-MS conditions were TSQ8000 mass spectrometer with a carrier gas of helium at a flow rate of 1 mL/min. The column used was Agilent HP-5 (30 m*0.25 mm, 0.25 μm). The GC-MS procedure was as the following: initial temperature 110° C. for 1 minutes; the temperature was raised to 120° C. at 10° C./min and maintained at 120° C. for 15 minutes; the temperature was further increased to 250° C. (10 minutes) at 20° C./min. The injection volume was 0.1 μl. The scanner used was Electronic shock wave 70 eV, with frequency at 1 scan/0.2 s and m/e at 40~400 units. The inlet temperature was 270° C., and the transmission line temperature was 280° C.

The composition of the product was analyzed by HPLC, such as Waters 1525 HPLC. The rate was 55:45:0.05 of the mobile phase of methanol:water:glacial acetic acid. The HPLC conditions were as the following: injection volume of 10 uL; the flow rate of 1 mL/min, the detection wavelength of 245 nm and the Column temperature of 30° C. The detector was DAD and the chromatographic column was Amethyst C18-H reversed column (5 μm, 4.6 mm×250 mm).

IR spectrum scanning identification of the product. With KBr tablet method, Nexus Fourier Transform Infrared spectrometer (test resolution≤0.5 cm$^{-1}$, the times of scanning 64 times, the test range of 378~4000 cm$^{-1}$) measured the infrared spectra of the sample.

Figure 1:
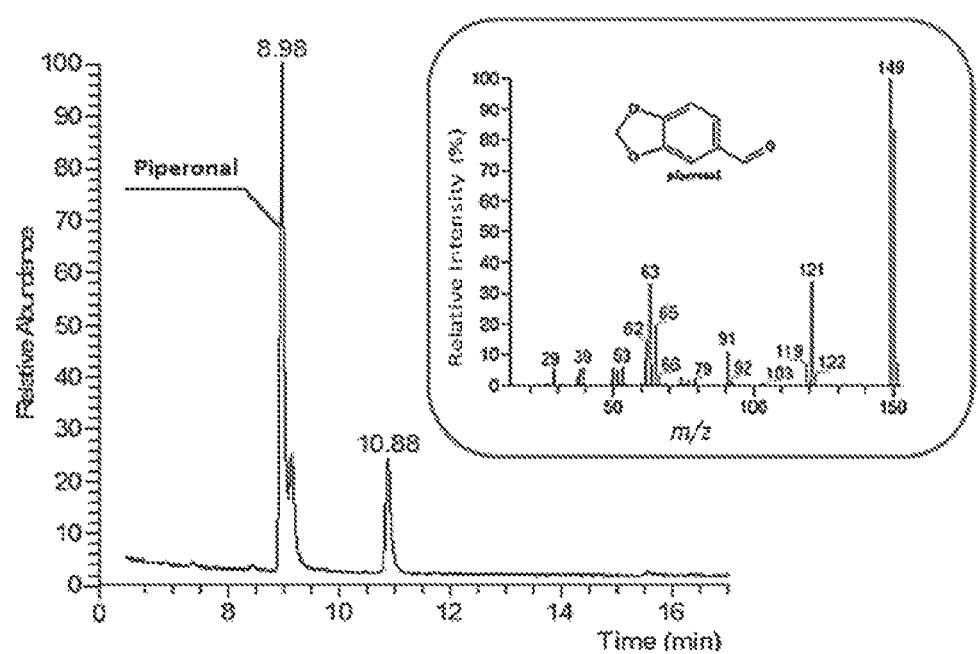
FIG. 1 shows the gas chromatography mass spectrometry (GC-MS) identification of the product.

Embodiment 1 Screening and Identification of the *Serratia liquefaciens* ZMT-1 Strain (1) Screening of Microbial Strains:

Twenty-five soil samples were collected from Xiamen, Wuxi, Fuyuan, Tibet Nyingchi, Hubei province and Henan provinces. After enrichment treatment, samples were spread on culture media plats. The samples were allowed to fully grow, after which 296 single colonies were picked and streaked on individual plates. At the end of the conversion, two microliter of the conversion solution was centrifuged to separate the cells from the solution. The resulting supernatant was collected and reacted with 2,4-dinitrophenylhydrazine until orange-red color appeared. The samples with the orange-red color had been re-screed. The strains to be re-screened were grown in test tube for 24-36 hours at 30° C. with a shaking speed of 150~220 rpm. Following cell growth, safrole was added to the cell culture at concentrations of 0.5-1.5 g/L for conversion from safrole to Heliotropin for 24~48 hours with the same temperature and rotation speed conditions. After the completion of the conversion, the re-screened strains were further analyzed with color reaction with the same procedure or high performance liquid chromatography (HPLC), gas phase analysis (GC) and GC-MS to identify the product; The strain ZMT-1 was selected as the strain that accumulated the most significant accumulation of Heliotropin. FIG. 1 shows the results of gas chromatography mass spectrometry (GC-MS) analysis of the conversion solution.

(2) Identification of the Microbial Strains

The strain ZMT-1 was identified morphologically and biochemically according to "Handbook of Industrial Microbial Techniques" and "Bergey's Manual of Determinative Bacteriology (1994)".

Morphological description of the strain: when grown on the basic inorganic salt plates, the colonies of ZMT-1 appear pale white, translucent and viscous. The colonies are about 1 mm in diameter, with middle raised and neat edges. Electron microscopy showed that the cells are about (0.5~0.8) μm×(0.5-2.0) μm in size and have a straight rod shape and apex obtuse. The cells of the *Serratia liquefaciens* ZMT-1 do not sporulate and do not form a capsule, but the cells have flagella. The strain ZMT-1 is facultative aerobic and Gram-negative. The strain ZMT-1 grows in conditions ranging from 10-37° C., pH 4-9 and 0-4% NaCl (w/v). The strain ZMT-1 is able to peptonize milk, liquefy gelatin, as well as produce catalase. The train ZMT-1 also makes urease reaction weakly positive, but the strain does not produce amylase and $H_2S$. The indole reaction is negative, while the nitrate reduction is positive. These remarkable physiological and biochemical characteristics show that the strain ZMT-1 is strongly tolerance to temperature, pH and NaCl.

The genomic DNA of the screened strain ZMT-1 was extracted by the Bacterial Genomic DNA Extraction kit (Shanghai Jierui Bioengineering Co., Ltd.) according to the manufacturer's protocol. The 16S rRNA gene was amplified via PCR using the bacterial universal primers (forward primer 27F: 5'-AGAGTTTGATCCTGGCTCAG-3' (SEQ ID NO:1); reverse primer 1492R: 5'-GGTTACCTTGT-TACGACTT-3' (SEQ ID NO:2)), and the amplified 16S rRNA gene was submitted to Shanghai Sangon Co. Ltd. for sequencing. The obtained sequence of the 16S rRNA gene was submitted to GeneBank with the accession number KU999993. The 16S rRNA gene sequence of the strain ZMT-1 was analyzed with the 16S rRNA gene sequence of related strain in GeneBank retrieved by BLAST search program on the NCBI website (Table 1). The results showed that the 16S rDNA gene sequence of the strain ZMT-1 was 98%-99% homologous to the 16S rDNA gene sequence of a number of *Serratia* strains in the GeneBank database. A total of 15 highly homologous strains were downloaded from http://rdp.cme.msu.ed for genetic analysis. The analysis showed that strain ZMT-1 has the closest genetic relationship with the typical strain *Serratia liquefaciens* ATCC 27592.

The strain ZMT-1 and the type strain *Serratia liquefaciens* ATCC 27592 are different in carbon source utilization (such as lactose, etc.) and M-R reaction, but the two strain are the same in V-P reaction. In the oxidase, contact enzyme, gelatin decomposition, nitrate reductase and indole experiment, the two strain are exactly the same. The ZMT-1 is a fermentative strain and arginine diahydrolase is negative, so it is not a *Serratia* format. The strain ZMT-1 also metabolizes arabinose to produce acid so it is not a *Serratia marcescens*.

In summary, the strain ZMT-1 is considered to be a *Serratia liquefaciens* strain and is given the name *Serratia liquefaciens* ZMT-1, which has been deposited since 5 Apr. 2016, in China Center of Typical Culture Collection with the accession number CCTCC NO: M 2016170.

TABLE 1

Homology analysis

| Strain name | NCBI number | Homology |
|---|---|---|
| *Serratia liquefaciens* ATCC27592 | NR_122057.1 | 99% |
| *Serratia liquefaciens* CZA1202 | KC191827.1 | 98% |
| *Serratia grimesii* PSB24 | HQ242737.1 | 98% |
| *Serratia grimesii* Cl-05 | KC178579.1 | 98% |
| *Serratia liquefaciens* CIP 103238 | NR_042062.1 | 97% |
| *Serratia grimesii* CNY-04 | KC167881.1 | 97% |
| *Serratia proteamaculans* OAct423 | KC514128.1 | 97% |
| *Serratia grimesii* DSM 30063 | NR_025340.1 | 97% |
| *Serratia grimesii* LMG 7883 | NR_114576.1 | 96% |
| *Serratia grimesii* NBRC 13537 | NR_113616.1 | 96% |
| *Serratia proteamaculans* 568 | NR_074820.1 | 96% |
| *Serratia proteamaculans* BZ56 | HQ588837.1 | 96% |
| *Serratia proteamaculans* DSM 4543 | NR_025341.1 | 96% |
| *Serratia quinivorans* LMG 7887 | NR_114575.1 | 96% |
| *Serratia* sp. HX-B01 | KF501474.1 | 95% |
| *Serratia* sp. QTYC33b | KM974657.1 | 95% |

TABLE 2

Physiological and biochemical characteristics

| Experiments | ZMT-1 | ATCC 27592 |
|---|---|---|
| Grow temperature | | |
| 22° C. | + | + |
| 37° C. | + | + |
| Light white | + | Not |
| Smell | No | Not |
| Oxidation type (O)/fermentation type (F) | F | F |
| Whether or not the following substances are used to produce acid | | |
| lactose | − | + |
| D-(+)-Glucose | + | + |
| sucrose | + | + |
| mannose | + | + |
| L-Arabia sugar | + | + |
| maltose | + | + |
| xylose | + | + |
| trehalose | + | + |

TABLE 2-continued

Physiological and biochemical characteristics

| Experiments | ZMT-1 | ATCC 27592 |
|---|---|---|
| Glycerin | + | + |
| mannose | + | + |
| Galactose | + | + |
| Nitrate reduction | + | + |
| oxidase | − | − |
| pigment | − | − |
| hydrogen sulfide test | − | − |
| Trypsin experiment | W | − |
| Indole experiment | − | − |
| Methyl red (MR) | − | + |
| V-P | + | + |
| Arginine dihydrolase expriment | − | − |
| Contact enzyme | + | + |
| Gelatin liquefaction | + | + |
| Glucose gas production | + | + |
| motility | + | + |
| Milk peptone | + | Not |

ATCC 27592 indicates *Serratia liquefaciens* ATCC 27592; +, indicates positive; W, indicates weakly positive; −, indicates negative.

Embodiment 2

With glucose as the single carbon source, the seed liquid of the strain ZMT-1 was used to inoculate in 6 trigonometric flasks with a capacity of 500 mL with 5% inoculation. The fermentation medium consisted of 1 g/L ammonium nitrate, 0.5 g/L magnesium sulfate heptahydrate, 0.5 g/L ammonium sulfate, 0.5 g/L potassium dihydrogen phosphate, 1.5 g/L dipotassium hydrogen phosphate, 0.5 g/L sodium chloride, 0.5 g/L yeast power and 5 g/L glucose. The pH of the fermentation medium was 6.8~7.5. The liquid volumes were 50 mL, 100 mL, 150 mL, 200 mL, 250 mL, 300 mL and 350 mL respectively. After growth for 24 hours under the conditions of 30° C. and 180 rpm shaking speed, the safrole substrate was added at a concentration of 0.9 g/L. With safrole added, the strain ZMT-1 was allowed to grow in the flasks for another 36 hours under the same culture conditions. The Heliotropin product concentrations were measured according to the liquid phase detection. The results are shown in Table 3.

TABLE 3

The effect of different liquid volume on the conversion

| | Liqiud volume(mL) | | | | | | |
|---|---|---|---|---|---|---|---|
| | 50 | 100 | 150 | 200 | 250 | 300 | 350 |
| 36 h Yield (mg/L) | 150 | 183 | 198 | 201 | 192 | 200 | 205 |
| 48 h Yield (mg/L) | 162 | 205 | 214 | 227 | 226 | 223 | 225 |

Embodiment 3

Five percent of the seed solution of the *Serratia liquefaciens* ZMT-1 was used to inoculate the fermentation media, which used glucose, fructose, mannitol, sucrose, glycerol or maltose as the carbon source respectively. Fermentation was carried out as in Embodiment 2 and the results are shown in Table 4 below.

TABLE 4

Utilization of different carbon sources

| Carbon source | Production (mg/L) |
| --- | --- |
| Glucose | 204 |
| Fructose | 191 |
| Mannitol | 167 |
| Sucrose | 196 |
| Glycerin | 171 |
| Maltose | 185 |

Embodiment 4

Figure 2:
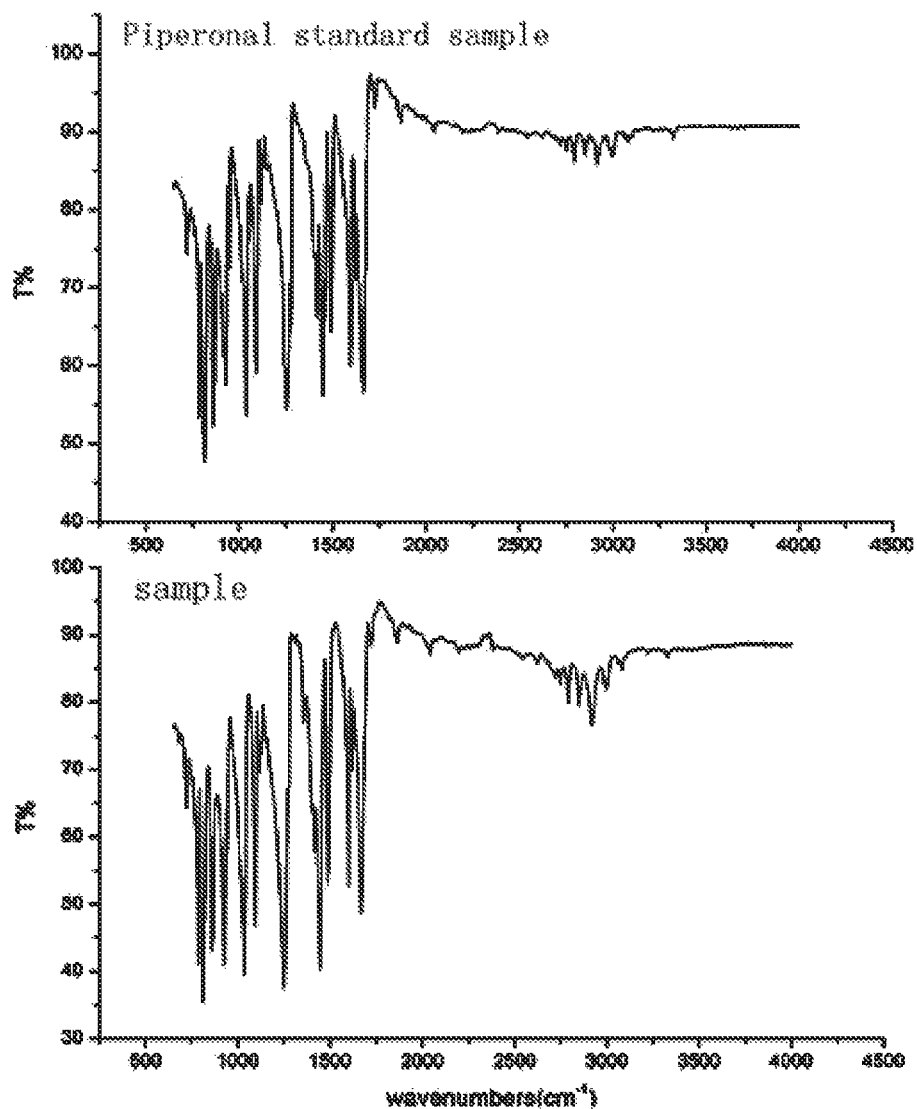
FIG. 2 shows the IR spectrum of the product.

With glucose as the single carbon source, five percent of the seed solution of the strain ZMT-1 was used to inoculate a 500 mL flask with 200 mL fermentation media. The incubated flask was incubated at 30° C. with 180 rpm rotation speed. After 30 hours incubation, the safrole substrate was added to the fermentation media at a conversion of 1.8 g/L. The final Heliotropin yield was 524 mg/L. The macroporous resin XAD-2 or HZ-802 was added to the conversion system at resin wet weight/conversion volume ratios of 5%-50% and the resin was shock-adsorbed for 30-60 minutes. The resin was filtered out and the filtrates were eluted with ethyl acetate of twice the resin volume. The elution process was carried out at 35-45° C. After elution, anhydrous sodium sulfate was added to the eluted filtrates and the filtrates were left to dry for 8-10 hours. The eluted filtrates were concentrated under the vacuum condition to a Heliotropin concentration of 250-300 g/L. The distillation bottle was rinsed with tap water for cooling. The concentrated liquid was then washed with cold water of 2 to 5 times the concentrated liquid volume. The concentrated liquid was left to crystallize in a 4° C. freezer. After drying at a low temperature, about 210 mg of a crystalline sample was obtained. FIG. 2 shows the infrared spectroscopy identification of the product, measured by infrared as Heliotropin.

While the invention has been described in ways of the aforementioned preferred embodiments, it is to be understood that the invention is not limited thereto. It is intended that all changes and modifications can be made without departing from the spirit and scope of the invention. The protection scope of the present invention should be defined by the claims.

The invention claimed is:

1. A method for producing Heliotropin from safrole, comprising:
   a) providing a catalytically effective amount of *Serratia liquefaciens* ZMT-1, CCTCC NO: M2016170, in a fermentation medium as a seed solution;
   b) adding the substrate safrole to the seed solution;
   c) culturing the seed solution for a length of time sufficient to make Heliotropin; and
   d) isolating the Heliotropin made in step (c).

2. The method for producing the Heliotropin according to claim 1, characterized in that, measured by volume, 2% to 10% of the said strain ZMT-1 seed solution is inoculated the fermentation medium with a loading volume of 10 to 40%; under the conditions of the temperature of 22-37° C. and the rotation speed of 150-220 rpm, the strain is cultured for 24-36 hours, after which the safrole substrate is added and converted under the same temperature and rotation speed for 24-48 hours.

3. The method for producing the Heliotropin according to claim 2, characterized in that the fermentation medium contains 0.5-1 g/L of ammonium nitrate, 0.1-0.5 g/L of magnesium sulfate heptahydrate, 0.1-0.5 g/L of ammonium sulfate, 0.1-0.5 g/L of potassium dihydrogen phosphate, 0.5-1.5 g/L of dipotassium hydrogen phosphate, 0.1-0.5 g/L of sodium chloride, 0.1-1 g/L of yeast powder and 3-20 g/L of glucose; the pH of the fermentation medium is 6.8-7.5.

4. The method for producing the Heliotropin according to claim 3, characterized in that the glucose can be replaced with one of fructose, mannitol, sucrose, glycerin and maltose.

5. The method for producing the Heliotropin according to claim 2, characterized in that the substrate is used with the concentrations of 0.5-3 g/L.

6. The method for producing the Heliotropin according to claim 2, characterized in that, measured by volume, 5% of the *Serratia liquefaciens* ZMT-1 seed solution is inoculated the fermentation medium with a loading volume of 20%; the ZMT-1 strain grows in the fermentation medium under the condition of 30° C. and 180 rpm for 24-36 hours, after which the safrole substrate is added and converted under the same temperature and rotation speed for 48 hours.

7. The method for producing the Heliotropin according to claim 2, characterized in that after the conversion is completed, to each 100 mL of conversion system, 5-50 gram of wet resin is added and shock-adsorbed for 30-60 minutes; the resin is a macroporous resin; the resin is filtered out and the filtrates are eluted ethyl acetate of 1 to 2 times the resin volume; the eluted filtrates are supplied with anhydrous sodium sulfate to dehydrate; the dehydrated filtrates are concentrated under vacuum condition at 30~50° C. and left to crystalize in a 4° C. refrigerator.

8. The method for producing the Heliotropin according to claim 3, characterized in that, measured by volume, 5% of the *Serratia liquefaciens* ZMT-1 seed solution is inoculated the fermentation medium with a loading volume of 20%; the ZMT-1 strain grows in the fermentation medium under the condition of 30° C. and 180 rpm for 24-36 hours, after which the safrole substrate is added and converted under the same temperature and rotation speed for 48 hours.

9. The method for producing the Heliotropin according to claim 4, characterized in that, measured by volume, 5% of the *Serratia liquefaciens* ZMT-1 seed solution is inoculated the fermentation medium with a loading volume of 20%; the ZMT-1 strain grows in the fermentation medium under the condition of 30° C. and 180 rpm for 24-36 hours, after which the safrole substrate is added and converted under the same temperature and rotation speed for 48 hours.

10. The method for producing the Heliotropin according to claim 5, characterized in that, measured by volume, 5% of the *Serratia liquefaciens* ZMT-1 seed solution is inoculated the fermentation medium with a loading volume of 20%; the ZMT-1 strain grows in the fermentation medium under the condition of 30° C. and 180 rpm for 24-36 hours, after which the safrole substrate is added and converted under the same temperature and rotation speed for 48 hours.

* * * * *